(12) United States Patent
Gershtein et al.

(10) Patent No.: US 8,616,075 B2
(45) Date of Patent: *Dec. 31, 2013

(54) SYSTEM FOR PERFORMING INSPECTIONS, REPAIRS, AND/OR OTHER OPERATIONS WITHIN VESSELS

(75) Inventors: Vladimir Yliy Gershtein, Allentown, PA (US); Andrew James Toth, New Tripoli, PA (US); Christopher R. Butler, Allentown, PA (US)

(73) Assignee: Air Products and Chemicals, Inc., Allentown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/106,430

(22) Filed: May 12, 2011

(65) Prior Publication Data

US 2012/0125128 A1 May 24, 2012

Related U.S. Application Data

(62) Division of application No. 11/944,669, filed on Nov. 26, 2007, now Pat. No. 7,971,497.

(51) Int. Cl.
*G01M 99/00* (2011.01)
(52) U.S. Cl.
USPC ........................................................ 73/865.8
(58) Field of Classification Search
USPC ........................................................ 73/865.8
See application file for complete search history.

(56) References Cited

U.S. PATENT DOCUMENTS

| | | | |
|---|---|---|---|
| 3,653,265 A | 4/1972 | Vallino et al. |
| 3,664,922 A | 5/1972 | Diwinsky |
| 3,708,064 A | 1/1973 | Schepler et al. |
| 3,715,914 A | 2/1973 | Gross et al. |
| 3,784,827 A | 1/1974 | Calhoun |
| 3,857,052 A | 12/1974 | Beller |
| 3,906,572 A | 9/1975 | Winn |
| 4,052,950 A | 10/1977 | Hirata |
| 4,311,556 A | 1/1982 | Iwamoto et al. |
| 4,385,318 A | 5/1983 | Miller |
| 4,391,373 A | 7/1983 | Wiggins |
| 4,432,013 A | 2/1984 | Miller et al. |
| 4,491,237 A | 1/1985 | Diggins |
| 4,560,931 A | 12/1985 | Murakami et al. |
| 4,696,544 A | 9/1987 | Costella |
| 4,883,576 A | 11/1989 | Gemma |

(Continued)

FOREIGN PATENT DOCUMENTS

CN 1695906 A 11/2005
EP 1 145 775 A2 10/2011

(Continued)

OTHER PUBLICATIONS

Solvay Solexis; "High Performance Fluoropolymer Coatings & Linings", Internet Citation, Jan. 1, 2006; pp. 1-16.

(Continued)

*Primary Examiner* — Hezron E Williams
*Assistant Examiner* — Nashmiya Fayyaz
(74) *Attorney, Agent, or Firm* — Rosaleen P. Morris-Oskanian

(57) ABSTRACT

A system is provided to facilitate inspections, repairs, and other operations within vessels without human entry into the vessels, and without introducing contaminants that could reduce the purity of materials held in the vessels below predetermined minimum levels.

19 Claims, 8 Drawing Sheets

(56) References Cited

U.S. PATENT DOCUMENTS

| | | | |
|---|---|---|---|
| 4,893,933 A | 1/1990 | Neiheisel et al. | |
| 5,205,174 A | 4/1993 | Silverman et al. | |
| 5,279,167 A | 1/1994 | Peterson | |
| 5,330,490 A | 7/1994 | Wilk et al. | |
| 5,388,707 A | 2/1995 | Stivison et al. | |
| 5,396,525 A | 3/1995 | Domy et al. | |
| 5,425,279 A | 6/1995 | Clark et al. | |
| 5,503,033 A | 4/1996 | Van Niekerk | |
| 5,604,532 A | 2/1997 | Tillmanns | |
| 6,104,970 A * | 8/2000 | Schmidt et al. | 701/2 |
| 6,525,333 B1 | 2/2003 | Hooker et al. | |
| 6,616,769 B2 | 9/2003 | Lachawiec, Jr. et al. | |
| 6,741,274 B1 | 5/2004 | Stevenson | |
| 6,814,092 B2 | 11/2004 | Lachawiec, Jr. et al. | |
| 6,929,142 B2 | 8/2005 | Gilbert | |
| 2002/0139840 A1 | 10/2002 | Madrid et al. | |
| 2004/0004551 A1 | 1/2004 | Early | |
| 2005/0008436 A1 | 1/2005 | Burnham et al. | |
| 2005/0252296 A1 | 11/2005 | Hock et al. | |
| 2006/0221877 A1 | 10/2006 | Belanger | |

FOREIGN PATENT DOCUMENTS

| | | |
|---|---|---|
| GB | 2 105 048 A | 3/1983 |
| GB | 2105048 A | 3/1983 |
| JP | 05-020881 A | 1/1993 |
| JP | 7-21547 B2 | 3/1995 |
| JP | 10-170448 A2 | 6/1998 |
| JP | 2000-145391 A2 | 5/2000 |
| JP | 2002-156307 A2 | 11/2000 |
| JP | 2004-055723 A | 2/2004 |
| JP | 2007-209391 A | 8/2007 |

OTHER PUBLICATIONS

IMDG International Maritime Dangerous Goods Code 2006 Edition, vol. 1.

CSC International Convention for Safe Containers, 1972, as amended, 5th Edition (1993.

Solvay Solexis; "High Performance Fluoropolymer Coatings & Linings"; Jan. 1, 2006; pp. 1-16; XP009156778.

* cited by examiner

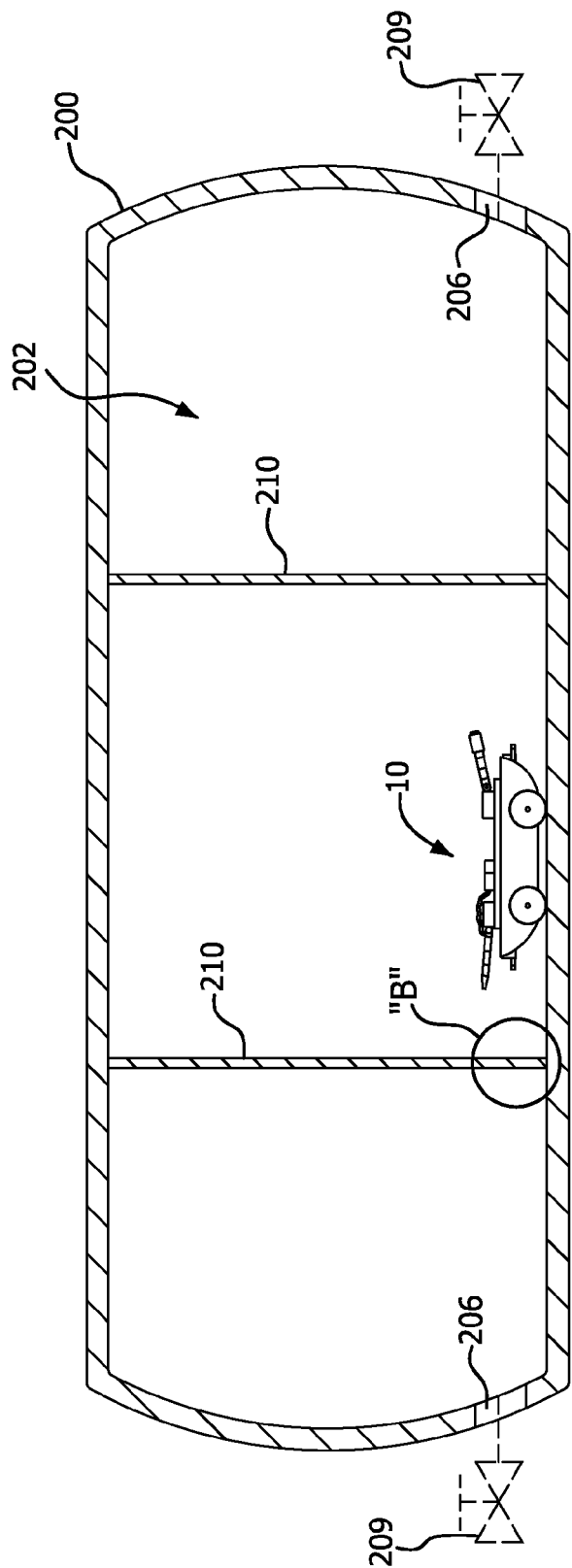
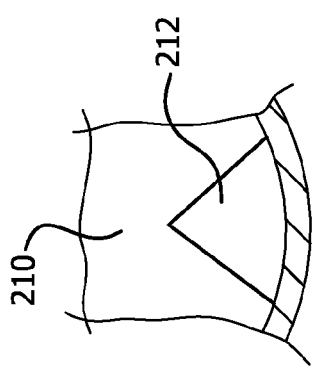
FIG. 4
FIG. 5

SYSTEM FOR PERFORMING INSPECTIONS, REPAIRS, AND/OR OTHER OPERATIONS WITHIN VESSELS

CROSS-REFERENCE TO RELATED APPLICATIONS

This application is a divisional application of U.S. application Ser. No. 11/944,669, filed Nov. 26, 2007, which is incorporated herein by reference in its entirety.

BACKGROUND OF THE INVENTION

The present invention relates to containers or vessels used to hold and ship specialty and other materials such as high-purity (HP) and ultra-high-purity (UHP) fluids. More particularly, the invention relates to devices and methods that can be used to inspect and/or repair interior areas of such vessels without the need for human entry into the vessels.

New developments and enhancements in technologies utilized in the electronics industry are leading to demands for increasing quantities of specialty materials such as HP and UHP fluids used in manufacturing processes. Specialty materials are chemicals used in manufacturing processes, such as the manufacture of electronic components, that exhibit certain properties such as high purity or ultra high purity. Specialty materials can be, for example, powders, emulsions, suspensions, and vapors. The term "fluids," as used herein, is intended to encompass gases, liquids, sublimed solids, and combinations thereof.

Specialty materials used for different processes and treatment of associated production equipment may require delivery of products with impurities measured at the ppb level. Even though specialty gases and chemicals may account for only about 0.01 to about 0.1 percent of production expenses, a shortage of these materials can jeopardize the ability to maintain desired or required production volumes in, for example, electronics manufacturing facilities. In some cases using contaminated product in a manufacturing process may jeopardize the final product specification, which may be determined at the very last stage of the manufacturing processes, for example product quality assurance in the case of wafer production. Produced wafers may be considered "out of spec" and may be thrown away, which accounts for the losses of many millions of dollars. Therefore, preserving the purity of specialty materials during delivery is of substantial importance.

Contamination of a vessel used to hold an HP or UHP fluid or other specialty material can be characterized as the presence of substances that can compromise a pre-defined purity level of the specialty material upon introduction of the specialty material into the vessel, or the penetration of the impurities into the vessel during transportation and/or storing of the high purity products in the vessel.

Contaminants can take the form of solids, liquids, and gases. Contaminants can be formed, for example, by residue from another type of material previously stored in the vessel. Contaminants can also be introduced by, for example, infiltration of ambient air into the internal volume of the vessel due to leaks in the vessel. More particularly, oxygen introduced by ambient-air infiltration is generally considered a contaminant with respect to HP and UHP fluids and other specialty materials used in the manufacture of electronics. The oxygen can form contaminating oxides on the interior surfaces of the vessel. Moreover, oxygen molecules can be trapped on the internal surfaces of the vessel, and can diffuse into the HP or UHP fluid or other specialty material which is subsequently placed in the vessel. As the HP or UHP fluid resides in a vessel, the oxygen molecules can be drawn out of the vessel internal surfaces due to a concentration gradient with the HP or UHP fluid and carried into the production facility, adversely affecting the final product specification.

Substances characterized as contaminants for a specialty material are application-dependent, and can vary with factors such as the specific type of specialty material, the product specification of the specialty material, and the intended use of the specialty material. Thus, a substance considered a contaminant in one application may not be considered a contaminant in other applications. For example, oxygen, hydrocarbons, metal particles, water, and nitrogen are considered contaminants of supercritical carbon dioxide ($scCO_2$). Nitrogen is not considered a contaminant, however, of electronics-grade gases such as $NH_3$, $NF_3$, and $Cl_2$.

In some cases, the older delivery methods for delivering small quantities of HP and UHP materials may no longer be applicable. For example, deliveries using cylinder bottles or other small packages may no longer be acceptable in some manufacturing processes due to the need for relatively large quantities of such materials. For example, demands for ultra-high purity "White Ammonia" ($NH_3$) and high purity nitrogen-triflouride ($NF_3$) have grown significantly in recent years, and bulk quantities of these materials are now required in many different manufacturing processes.

Bulk delivery vessels and systems for delivering HP and UHP materials were not known or used in the recent past. Only the recent development of new technologies, for example, technologies used for production of various electronic devices, have lead to the demand for large quantities of HP and UHP products such as $NF_3$, $NH_3$, $CL_2$, HCl, and other specialty gases and chemicals. Small containers such as bottle cylinders were used in the past for delivery of relatively small quantities of HP and UHP products. Requirements for the preparation of small containers, while stringent, can be met relatively easily. Indeed, container preparation procedures for relatively small containers and vessels which are used to transport HP and UHP products are well known. For example, a simple container heating process in an oven, known as "baking," helps to achieve the required purity of container internal surfaces. Prepared or so called "purity treated" containers may receive UHP products without the threat of contaminating the UHP products. "Baking" ovens used for container heating may vary in size and shape, but typically are restricted to the preparation of relatively small containers such as cylinders.

Large size containers or vessels, such as those necessary for the delivery of industrial gases in bulk quantities, cannot utilize the preparation methods for relatively small containers. New container preparation methods for bulk HP and UHP products have been developed and introduced to the container industry. For example, preparation of ISO containers of about 6,000-pound capacity is described in U.S. Pat. Nos. 6,616,769B2 and 6,814,092B2, titled "Systems and Methods for conditioning Ultra High Purity Gas Bulk Containers." The preparation of these containers is much more complex than the preparation of smaller containers because the larger containers are too large to fit into existing "baking" ovens, and also because maximum surface temperature of the containers is regulated by national transportation bodies such as, for example, the U.S. Department of Transportation (DOT), the United Nations (UN), International Maritime Dangerous Goods (IMDG), European Agreement concerning the International Carriage of Dangerous Goods by Road (ADR), Convention for Safe Containers (CSC), etc. In other words, large containers used as transport vessels are regulated by transportation organizations around the world. For example, according to DOT recommendations, the maximum outside temperature of a portable ISO tank T50 type should not exceed 125° F., to avoid introducing thermal stresses and fatigue in tank. Apparently, a "baking" process cannot be performed since baking requires significantly higher temperatures to achieve adequate container surface preparation.

Methods for cleaning and preparing large size vessels for delivery of HP and UHP products are known and are in practice in the industry. These methods are quite involved and require significant effort and expense. Therefore, preservation of container purity is essential, and may significantly influence both delivered HP or UHP product revenue and quality of the devices produced using the delivered HP or UHP materials. For example, various steps of the manufacturing process for semiconductor wafers may rely on the use of delivered HP and UHP substances such as $NF_3$, $NH_3$, $CO_2$, etc.

Significant effort has been undertaken to develop and implement delivery systems and means for HP and UHP materials in bulk quantities. One of the important challenges associated with these deliveries has been the design and preparation of bulk containers in a way that these containers may be used to transport and deliver the required product purity without jeopardizing the latter. Some unique vessel designs and preparation procedures are known today. The task of container design and preparation to satisfy the handling of high purity substances is somewhat less complex in the case of stationary containers. For portable containers, however, the task of achieving and preserving product purity is more challenging. Portable containers need to comply with various regulations imposed not only by standards regulating container materials, design, and mechanical properties, but also by different national transportation bodies around the world including, for example, DOT, UN, IMDG, ADR, CSC, etc. The job of these bodies and their regulations is to make sure that portable containers carrying bulk quantities of different materials do not impose danger to the surrounding world during the transportation process. Container design, inspection, transportation, and other handling procedures are strictly regulated, and all containers that fail to comply with existing regulations are not permitted to be used for transporting dangerous goods. At the same time, some of the container design, preparation, and inspection procedures contradict high purity product requirements.

One would need to understand the requirements that are imposed on transportable containers to understand what may and may not be done to a standard container design, a regulated container preparation process, an inspection procedure, etc. New or modified container designs, as well as new or modified preparation and inspection procedures may need to be approved for use by national transportation bodies. An example of some of the inspection-related requirements imposed on containers is shown in the section "ISO Inspection Requirements" of ITCO ACC MANUAL issue No. 3: January 2003, which states: "[f]or man entry it is the responsibility of depot supervisor to ensure that the tank is safe to enter. This may require an inspection for gas contamination of low oxygen." This statement taken from the container inspection manual means that in the case of man entry to the tank (container), appropriate conditions are required to ensure that no hazardous gas residue is left inside the container, and the oxygen deficient atmosphere is eliminated. The latter may require an air purge if the container which may be a source of major container contamination forming, for example, metal oxides and other undesirable residue. In addition, a thorough container preparation (decontamination) procedure will be required to eliminate residual oxygen even after the container is purged with inert gas. Container surfaces may trap significant amount of oxygen which would be enough to contaminate a UHP product subsequently introduced into the container. An example of a quite involved container preparation method is described, for example, in U.S. Pat. No. 6,616, 769B2. Thus, a substantial amount of time, energy, and money can be saved by avoiding the need for container preparations whenever possible.

Another example of regulated container inspection requirements may be found in chapter "Pressure Vessel Not Acceptable Conditions" of the ITCO ACC MANUAL issue No. 3: January 2003. For example, the following vessel conditions found during the inspection may qualify the inspected vessel as unacceptable for further use:

defects to welds or parent materials
  body executed grinding, deeper than 0.1 mm (0.004 inch)
  Excessive grinding or other metal depletion which reduces the shell thickness to less than the minimum
  Corrosion or pitting which results in an shell thickness below the required minimum or create contamination traps
  Stress corrosion
  Sharp indentations, creases, or dents
  Dents grater then 6 mm (0.25 inch) to the top third of the tank shell
  Dents grater then 10 mm (0.4 inch) to the bottom two thirds of the tank shell To comply with the above-listed conditions, a rigorous internal container inspection is required. The inspection may involve not only visual qualitative analyses of the container internal surfaces, but also the actual measurement of possible surface discontinuities, particle sizes, shape of the internal structure, etc. Under today's standard practices, human entry into an inspected vessel is practically inevitable in order to achieve the required inspection quality. That is why the industry accepted and established standard requires a container entry by an inspector through the manway associated with internal container inspections. Thus, the size of a manway, and often its position as well, are regulated to ensure safe entry and exit into and out of a confined space by the inspector.

Another document which establishes requirement for containers shipped around the world has been developed by the UN. For example, UN type T50 Portable ISO Tanks used in International transport for the carriage and use of anhydrous Ammonia UN 1005. These are portable tanks meeting the definition of container in the International Convention for Safe Containers (CSC), 1972, as amended, and are subject to inspection and test in accordance with UN Model Regulations 6.7.3.15 et al. and the CSC. The document imposes strict requirement on conducting container inspections, as well as prescribing stringent time requirements for conducting these inspections. For example, the document states: " . . . A portable tank may not be filled after expiration of the last 2.5 or 5 year test date. A tank filled within the test date may be transported up to 3 months beyond the date of expiry of the last periodic test date . . . " Apparently, containers which have not had the inspection completed on time or have not passed the inspection may not be used for delivery of goods internationally. In the United States, similar regulations developed by DOT. The CSC regulations on container inspection and maintenance are addressed in the CSC regulation #2. For example: " . . . The first examination must occur no later than 5 years after production and then at least every 2.5 years thereafter . . . " In addition, the inspection regulations like CSC specify who may perform the inspection. The presence of qualified and licensed representatives is essential, and only these representatives may perform the inspection and eventually pass or fail the container for further use. The following is also stated in another section of the CSC document: "... The inspection and tests described herein must be performed or witnessed by an inspector/agency qualified and approved by the competent authority or its authorized body. The CSC and the UN tank test and inspection may be performed by the same inspector if they are suitably qualified to do so. Typical agencies approved to perform this work are: ABS, Bureau Veritas, Lloyds Register etc. . . . " In practice, the requirements in the last example demand that a qualified inspector should enter the container and perform the inspection. The final verdict on whether the container may continue to be used in service may be issued only upon completion of the inspection. Unfortunately, none of the qualified inspection agencies are intimately familiar with requirement for containers and systems transporting and supplying HP and UHP products. Therefore, the inspectors may be qualified to perform the inspection of the containers, but they may not be qualified to enter the container transporting HP or UHP goods.

An ongoing need therefore exits for devices and methods for performing internal inspections and repairs on vessels used to hold and HP and UHP fluids and other specialty products, without human entry into the vessel.

BRIEF SUMMARY OF THE INVENTION

Devices and methods facilitate inspections, repairs, and other operations within vessels without human entry into the vessels, and without introducing contaminants that could reduce the purity of materials held in the vessels below predetermined minimum levels.

Embodiments of devices are provided for performing operations within a vessel used to hold a first material having a predetermined minimum purity. The devices comprise a body; a wheel and/or a track movably connected to the body and supporting the device on a surface of the vessel while the device performs the operations within the vessel; and a shell mounted on the body and positioned at least in part between the body and the surface of the vessel while the device performs the operations within the vessel. The shell and the wheel and/or track are formed from one or more materials that do not reduce the purity of the first material below the predetermined minimum when the first material is exposed to the one or more materials.

Embodiments of systems are provided for obtaining information relating to the interior of a vessel. The systems comprise a device capable of entering the interior of the vessel. The device comprises: a body; a sensor mounted on the body; at least one of a transmitter for transmitting the information from the device and a memory-storage device for storing the information; and a shell that at least partially encloses the body and is capable of catching debris and particulate matter from other parts of the device.

Methods comprise providing a device configured to operate in the presence of a first material having a predetermined minimum purity without reducing the purity of the first material below the predetermined minimum; inserting the device into an internal volume of a vessel configured to hold the first material; and inspecting and/or repairing the vessel using the device.

Methods for inspecting a vessel having an internal volume comprise providing a device comprising a sensor; removing a valve from an opening formed in a shell of the vessel; introducing the device into the internal volume by way of the opening; and obtaining information concerning the vessel from the sensor.

BRIEF DESCRIPTION OF SEVERAL VIEWS OF THE DRAWINGS

The foregoing summary, as well as the following detailed description of preferred embodiments, are better understood when read in conjunction with the appended drawings. The drawings are presented for illustrative purposes only, and the scope of the appended claims is not limited to the specific embodiments shown in the drawings. In the drawings:

FIG. 4 is a side view of the device shown in FIGS. 1-4, depicting the device within an internal volume of a vessel, and depicting the vessel in longitudinal cross section;

FIG. 5 is a magnified view of the area designated "B" in FIG. 4, from a perspective rotated approximately ninety degrees from the perspective of FIG. 4;

DETAILED DESCRIPTION OF THE INVENTION

Figure 1:
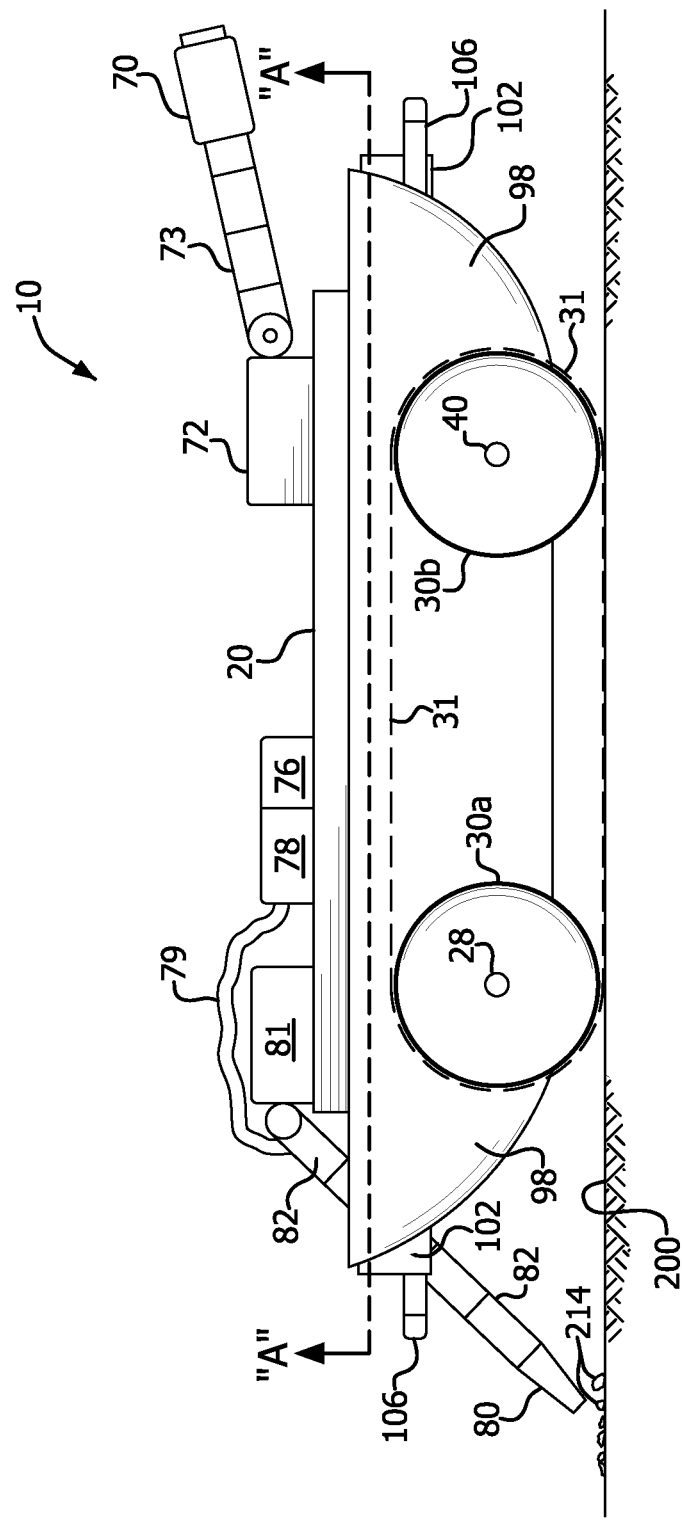
FIG. 1 is a side view of an embodiment of a device for performing inspections, repairs, and/or other operations within vessels.

FIGS. 1 to 4, 8, and 10 depict an embodiment of a device 10. The device 10 can be used to inspect and/or repair an interior of a container or vessel 200. The vessel 200 defines an internal volume 202 that can be used to hold a UHP fluid such as ammonia ($NH_3$) at a purity of 99.999 percent or greater (hereinafter referred to as "UHP ammonia"). The vessel 200 and the internal volume 202 are depicted in FIG. 4. The device 10, as discussed below, is configured to operate in the internal volume 202 without introducing contaminants that could render the vessel 200 unsuitable for storing the UHP ammonia.

The use of the device 10 in connection with a vessel 200 used to hold UHP ammonia is described for exemplary purposes only. The device 10 can also be used to inspect the interiors of vessels used to hold materials other than ultra-high purity gases.

The device 10 is sized to fit inside, and maneuver within the vessel 200. For example, the vessel 200 has openings 206 in the exterior shell 208 thereof. Each opening 206 accommodates a pressure-relief valve 209 (depicted in phantom in FIG. 4). The vessel 200 also includes internal baffles 210 that divide the internal volume 202 into compartments. The baffles 210 each include, for example, a V-shaped opening 212, as shown in FIG. 5. The device 10 needs to be small enough to fit within at least one of the access openings 206 (when the associated pressure relief-valve 209 is removed) and the V-shaped openings 212, so that the device 10 can access all of the compartments within the internal volume 202.

Figure 3:
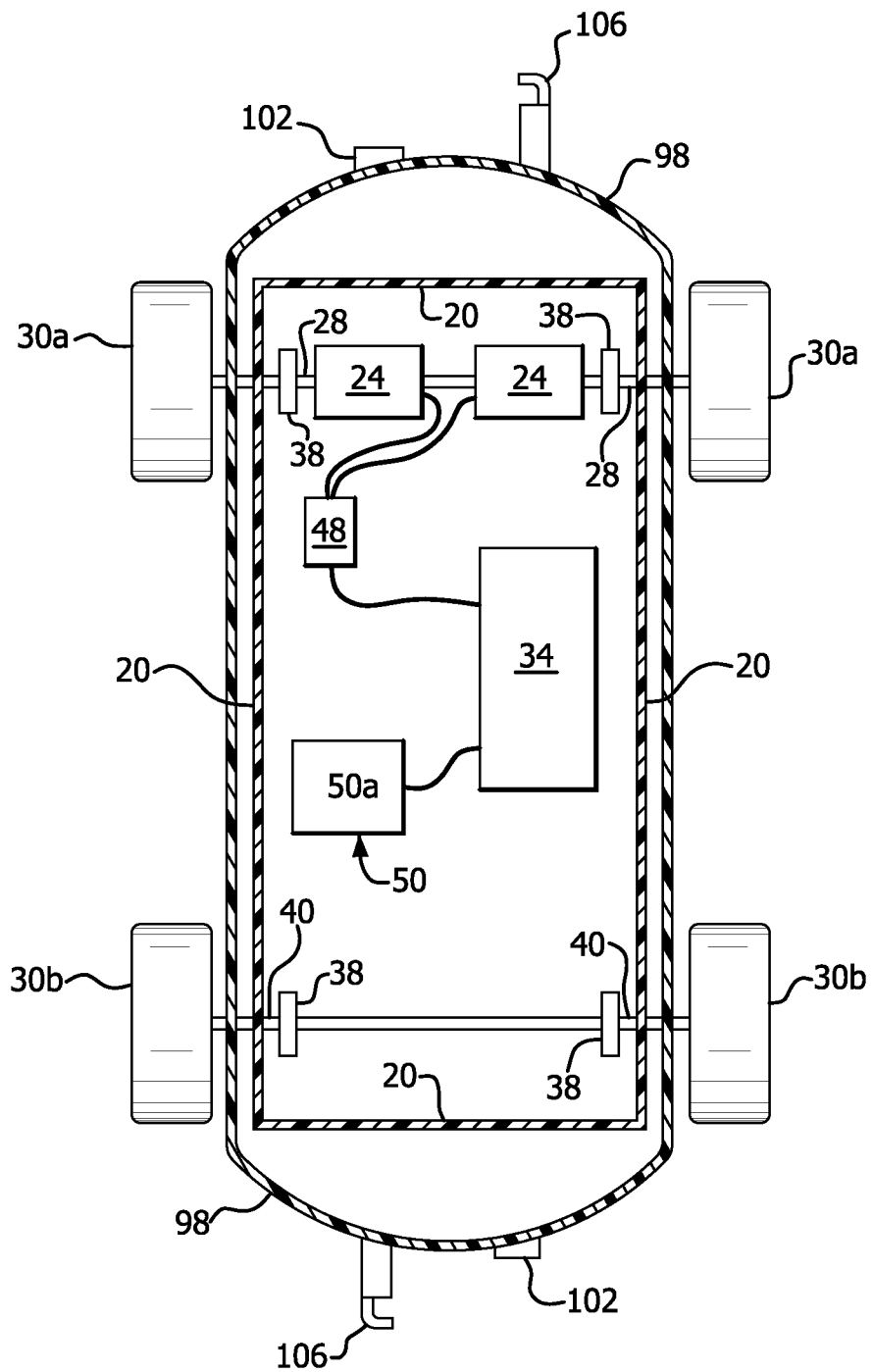
FIG. 3 is a top cross-sectional view of the device shown in FIGS. 1 and 2, taken through the line "A-A" of FIG. 1.

The device 10 comprises a body 20 and two motors 24 each mounted on the body 20, as shown in FIG. 3. The device 10 also includes two drive axles 28, and two wheels 30a each mounted on a respective one of the drive axles 28. The term "wheel," as used through the specification and claims, is intended to encompass rollers, disks, drums, circular frames, etc.

Each drive axle 28 is connected to a respective one of the motors 24 so that each motor 24 drives, or rotates one of the wheels 30a. Alternative embodiments can be equipped with one motor that drives both of the wheels 30a. Other alternative embodiments can include more than two drive axles 28, two motors 24, and two wheels 30a. Moreover, alternative embodiments can be equipped with tracks in lieu of, or in addition to the wheels 30a. Tracks that can be used in alternative embodiments of the device 10 are depicted in phantom in FIG. 1, and are denoted by the reference character 31.

The motors 24 can be electric motors, to avoid introducing exhaust-related contaminants such as hydrocarbons, water vapor, particulate matter, etc. into the volume 202. The device 10 can include a battery 34 to power the motors 24 and the other electrical components of the device 10.

Figure 6:
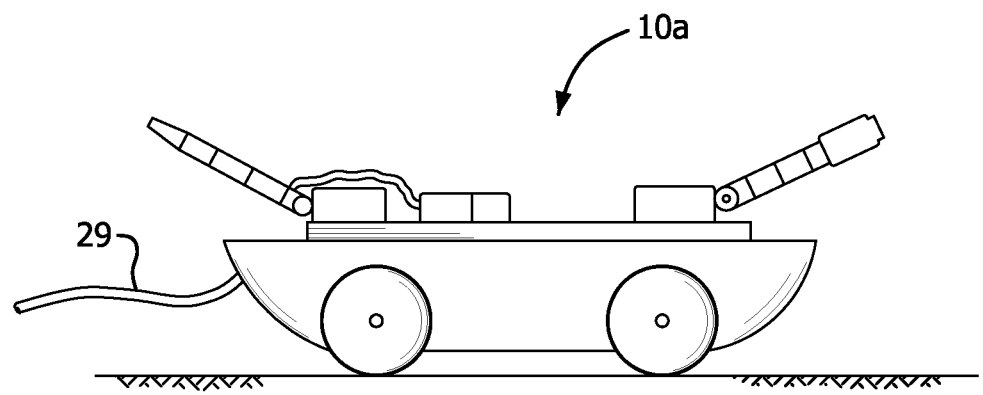
FIG. 6 is a side view of an alternative embodiment of the device shown in FIGS. 1-4.

An alternative embodiment in the form of a device 10a is depicted in FIG. 6. The device 10a is substantially identical to the device 10 with the following exception, and the other exceptions noted hereinafter. The device 10a includes a cable 29 that can be used to transmit electric power to the device 10a from a power source located outside of the vessel 200, thereby eliminating the need for a battery.

The wheels 30a can be formed from a material that will not contaminate the UHP ammonia (or other specialty material) to be stored in the vessel 200, i.e., the material from which the wheels 30s are formed will not lower the purity of the UHP ammonia below a predetermined minimum if the UHP ammonia comes into contact with the material. This feature can help to avoid contamination of the gas in the vessel 200 if particles of the material become liberated from the wheels 30a while the device is in the internal volume 202, and remain in the internal volume 202 thereafter. Moreover, the hardness of the material from which the wheels 30a are formed can be less than that of the material from which the vessel 200 is formed. This feature can help to ensure that any material liberated by contact between the wheels 30a and the vessel 200 consists substantially of material from the wheels 30a rather than the vessel 200.

For example, the wheels 30a can be formed from polytetrafluoroethylene (PTFE) or white silica material, since PTFE and white silica material will not contaminate this UHP ammonia. Moreover, PTFE and white silica each have a hardness that is less than that of the metallic materials commonly used to form vessels such as the vessel 200.

Each of the drive axles 28 can be coupled to the body 20 by way of a respective bushing 38 that permits the drive axle 28 and the attached wheel 30a to rotate in relation to the body 20, as shown in FIG. 3. Bearings can be used in lieu of the bushings 38 in alternative embodiments.

The device 10 can also include an axle 40, and two wheels 30b each mounted on respective ends of the axle 40. The wheels 30b can be substantially identical to the drive wheels 30a. Two additional bushings 38 can be used to couple the axle 40 to the body 20 so that the axle 40 can rotate in relation to the body 20.

The device 10 can also include a processor 48, as shown in FIG. 3. The processor 48 can be, for example, a microprocessor; other type of processors can be used in the alternative.

Figure 7:
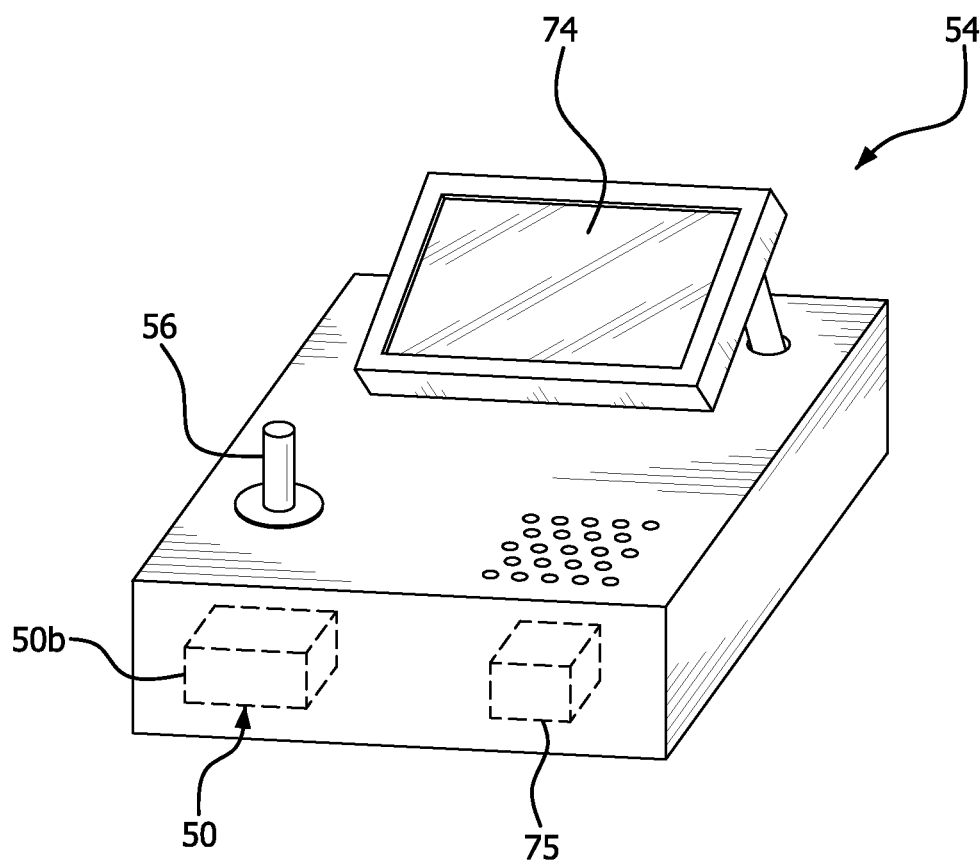
FIG. 7 is a perspective view of an operator console that can be used in conjunction with the device shown in FIGS. 1-4.

The device 10 can also include a telemetry system 50 for transmitting information between the device 10 and an operator module 54 located outside of the vessel 14. The operator module is depicted in FIG. 7. The telemetry system 50 can include a first transceiver 50a mounted on the body and communicatively coupled to the processor 48, as shown in FIG. 3. The telemetry system 50 can also include a second transceiver 50b that forms part of the operator module 54. The first and second transceivers can communicate by, for example, radio frequency (RF) transmission; other types of communication protocols can be used in the alternative.

Information can be transmitted between the device 10 and the operator console 54 by way of the cable 29 in the alternative device 10a, thereby eliminating the need for a telemetry system.

The processor 48 can control the operation of the motors 24 to effectuate movement of the device 10 in a desired direction. More particularly, each of the motors 24 can be electrically connected to the battery 34 by way of the processor 48, so that the processor 48 can selectively activate, deactivate, and reverse each motor 24 in response to inputs received from the operator by way of the telemetry system 52. The operator inputs can be generated using a joystick controller 56 or other suitable device that forms part of the operator module 54.

The motors 24 can be activated simultaneously in the same direction in response to inputs from the operator, to facilitate linear movement of the device 10 in the forward or rearward directions.

The device 10 can be steered using differential movement between the wheels 30a. More particularly, the device can be steered by activating one of the motors 24 while the other motor 24 is deactivated; by activating the motors 24 in opposite directions; or by operating the motors 24 in the same direction, at different speeds.

Alternative embodiments can be equipped with a steering mechanism to turn the wheels 30b. Alternative embodiments can also be equipped with an additional two of the motors 24 to drive the wheels 30b.

Figure 2:
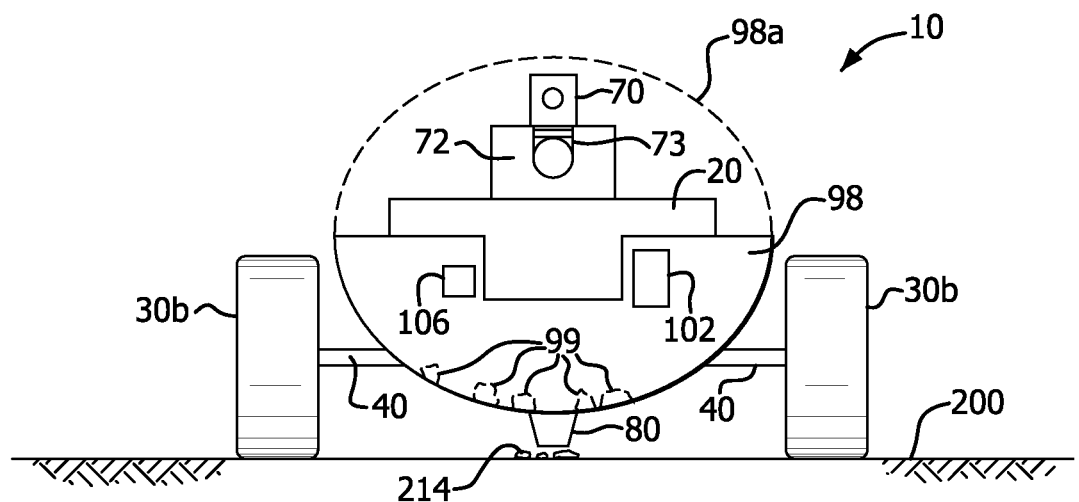
FIG. 2 is a front view of the device shown in FIG. 1.

The device 10 can also include one or more sensors mounted on the body 20 and communicatively coupled to the microprocessor 48. The sensor or sensors can be any device or devices suitable for performing the specific inspection task or tasks required in a particular application. For example, the device 10 is equipped with a video camera 70, as shown in FIGS. 1 and 2. The video camera 70, when used in conjunction with a suitable display, is capable of generating three-dimensional images. The device 10 can thus be used to visually inspect the interior of the vessel 200 for debris, cracks, gouges, improper assembly of piping and other components, and other potential problems. The camera 70 can also be used to identify the presence of debris within the vessel 200, such as particles 214 shown in FIGS. 1 and 2.

The device 10 can be configured to map the specific locations within the vessel 200 at which a defect or other problem is identified. For example, the device can be equipped with an infrared distance-measuring instrument (not shown), and the processor 48 can be programmed with mapping software that permit the device 10 to map the coordinates of the defect or other problem in relation to a predefined surface or other feature within the vessel 200.

Other types of sensors can be used in addition to, or in lieu of the camera 70 to obtain the information required in a particular application. For example, alternative embodiments the device 10 can be equipped with acoustic, infrared, X-ray, ultraviolet, or other types of sensors.

The video camera 70 can be mounted on the body 20 using a motorized mount 72 and a telescoping arm 73, as shown in FIGS. 1 and 2. The mount 72 permits the camera 70 to be panned and tilted in relation to the body 20, in response to operator inputs relayed from the operator console 54 by way of the telemetry system 50. The telescoping arm 73 permits the camera 70 to be moved toward or away from the mount 72 in response to additional operator inputs relayed by way of the telemetry system 50. Alternative embodiments can be configured with a fixed mount and/or a non-telescoping arm for the camera 70.

The video camera 70 can be communicatively coupled to the first transceiver 50a, so that the output of the camera 70 can transmitted to the operator module 54 and displayed on a real-time basis using a video monitor 74 or other suitable device. The operator module 54 can also include a memory-storage device 75 to record the output of the video camera 70 and any other sensors on the device 10.

Alternative embodiments of the device 10 can include an on-board memory-storage device communicatively coupled to the camera 70 and the other sensors on the device 10, to permit the outputs of the camera 70 or the other sensor to be stored and subsequently downloaded after the device has been retrieved from the vessel 200.

The device 10 can be equipped with a means for collecting material from the interior of the vessel 200. This feature can be used in applications where, for example, it is desired to remove some or all of the particulate matter found within the vessel 200 during the inspection process. A sample of the material can subsequently be analyzed to determine whether the material is a contaminant with respect to the UHP ammonia or other specialty material to be stored in the vessel 200.

The collecting means can include, for example, a vacuum source 76, a collection chamber 78 in fluid communication with the vacuum source 76, and a vacuum pickup 80 in fluid communication with the collection chamber 78 by way of a vacuum line 79, as shown in FIG. 1.

The vacuum pickup 80 can be mounted on the body 20 using a motorized mount 81 and a telescoping arm 82. The mount 82 permits the vacuum pickup 80 to be swept and tilted in relation to the body 20, in response to operator inputs relayed from the operator console 54 by way of the telemetry system 50. The telescoping arm 82 permits the vacuum pickup 80 to be moved toward or away from the mount 81 in response to additional operator inputs relayed by way of the telemetry system 50. Alternative embodiments can be configured with a fixed mount and/or a non-telescoping arm for the vacuum pickup 80.

The particles 214 located within the vessel 200 and identified using the camera 70 or other sensing device can be collected by positioning the device 10 so that the end of the pickup 80 is located proximate the particles 214, as shown in FIG. 1. The vacuum source 76 can then be activated so that the resulting vacuum causes the particles 214 to be sucked into the pickup 80 and deposited in the collection chamber 78. The particles 214 can be retrieved from the collection chamber for inspection and analysis after the device has been retrieved from the vessel 200.

The vacuum source 76 and the vacuum pickup 80 can also be used to verify that suspected particulate matter identified by the camera 70 or other sensor is indeed particulate matter and not a crack, gouge, or other imperfection in the vessel 200, without actually collecting the suspected particulate matter. More particularly, the device 10 can be maneuvered so that the vacuum pickup 80 is located near the suspected particulate matter. The vacuum source 76 can be activated, and the operator can monitor via the camera 70 whether the suspected particulate matter moves in response to the vacuum. The absence of any movement in response to the vacuum can be interpreted as an indication that the suspected particulate matter is actually an imperfection in the vessel 200 rather than particulate matter.

The device 10 can be equipped with a stationary or movable arm (not shown) or other suitable means for moving suspected particulate matter. This technique can be used lieu of attempting to move the suspected particulate matter using the vacuum source 76 and vacuum pickup 80.

The cable 29 of the alternative device 10a can include a vacuum line that places the vacuum pickup 80 on the device 10a in fluid communication with a vacuum source located outside the vessel 200. This feature can eliminate the need for a vacuum source and a collection chamber located on the device 10a.

Figure 8:
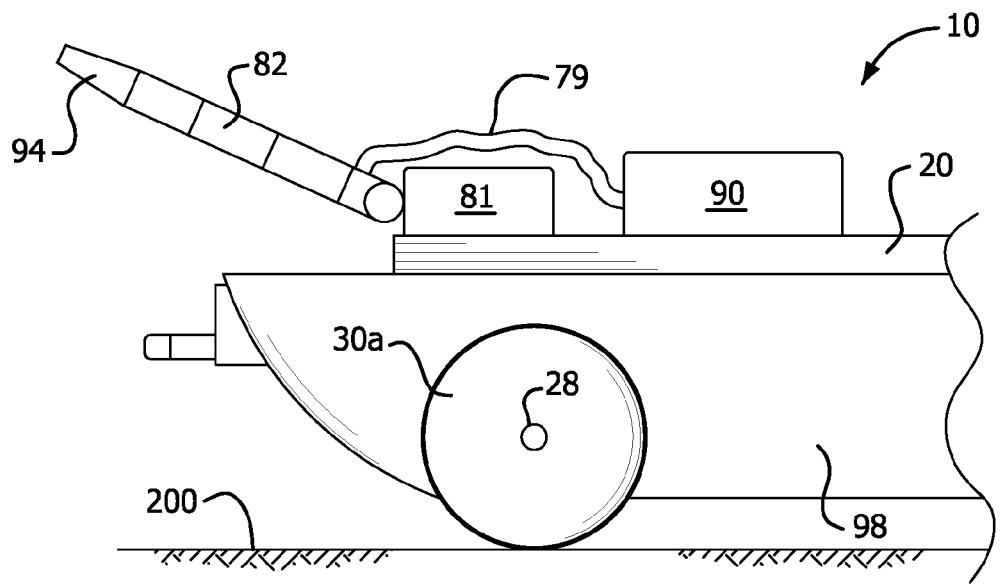
FIG. 8 is a side view of the device show in FIG. 1-4, configured to perform a repair operation within the vessel shown in FIG. 4.

The device 10 can also be configured to perform repairs within the vessel 200. For example, in certain applications, the vessel 200 can have a coating on its interior surfaces to protect the surfaces from corrosion or other detrimental effects caused by the material being held vessel 200. The device 10 can be used, for example, to re-coat areas in which the coating is found to be scratched, missing, or otherwise compromised. In particular, the device 10 can be equipped with a pressurized reservoir 90 of coating material. The reservoir 90 can be mounted on the body 20 in place of the vacuum source 76 and the collection chamber 78, as shown in FIG. 8. A spray nozzle 94 can be mounted on the telescoping arm 82 in lieu of the vacuum pickup 80.

The arm 82 and the mount 81 can be manipulated so that the spray nozzle 94 is located near the area in which the coating has been compromised. The coating material can be fed to the spray nozzle 94 from the reservoir 90 by way of the line 79 and arm 82, and sprayed onto the compromised area to re-coat the area.

The above-described re-coating operation is disclosed for exemplary purposes only; the device 10 can be configured to perform other types of repair operations.

The device 10 can also include a shell 98. The shell 98 is mounted on the body 20 so that the shell 98 is positioned between the body 20 and the underlying surface of the vessel 200, as shown in FIGS. 1-3. The shell 98 can catch particulate matter, grease, oil, and other potential contaminants that may be emitted by the device 10 during operation. Potential contaminants captured by the shell 98 are depicted in phantom and denoted by the reference character 99 in FIG. 2. The contaminants 99 can result from, for example, friction between the various moving and non-moving parts of the device 10, vibration or mechanical shocks which the device 10 may experience, lubricants used within the device 10, etc. The contaminants 99 captured by the shell 98 are removed from the internal volume 202 of the vessel 200 as the device 10 is retrieved.

The shell 98 can be made from a material that is compatible with the UHP ammonia (or other specialty material) which is to be stored within the vessel 200, i.e., the shell 98 can be formed from a material that will not lower the purity of the UHP ammonia below a predetermined minimum if the UHP ammonia comes into contact with the material. This feature can reduce the potential for the UHP ammonia to become contaminated if pieces of the shell 98 become liberated as the device 10 is operated within the internal volume 202.

Moreover, the hardness of the material from which the shell 98 is formed can be less than that of the material from which the vessel 200 is formed. This feature can help to ensure that any material liberated by inadvertent contact between the shell 98 and the vessel 200 consists substantially of material from the shell 98 rather than the vessel 200.

Also, the hardness of the material from which the shell 98 is formed can be less than that of the material from which the axles 28, 40 of the device 10 are formed. This feature can help to ensure that any material liberated by rubbing or other contact between the shell 98 and the axles 28, 40 consists substantially of material from the shell 98 rather than the axles 28, 40.

Alternative embodiments can be equipped with a shell 98a that completely encloses the body 20. The shell 98a is partially depicted in phantom in FIG. 2. Moreover, the shells 98, 98a are depicted with substantially curvilinear shapes for exemplary purposes only; alternative embodiments can have shells of other shapes.

Figure 9:
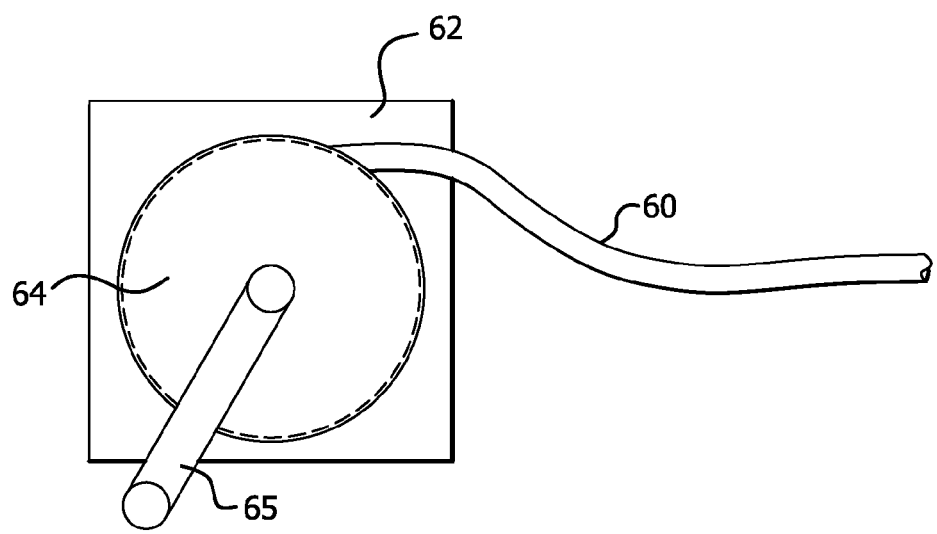
FIG. 9 is a side view of a tether that can be used to retrieve the device shown in FIGS. 1-4 and 8 from the vessel shown in FIG. 4, and a spool and a housing that can be used to store the tether, with half of the housing removed.

The device 10 can be equipped with provisions to retrieve the device 10 from the internal volume 202 of the vessel 200 if the device 10 becomes disabled or is otherwise unable to exit the interior volume 202 using its normal drive and steering capabilities. For example, the device 10 can be equipped with a tether 60. The tether 60 can be attached to the body 20 or other component of the device 10 before the device 10 enters the vessel 200. The tether 60 can be stored within a housing 62, and can be wound on a reel or spool 64 mounted within the housing 62. Half of the housing 62 is removed in FIG. 9, to reveal the spool 64.

The housing 62 and the spool 64 remain outside of the vessel 200. The tether 60 unwinds from the spool 64 as the device 10 moves into and through the vessel 200. The movement of the device 10 away from the housing 62 and the spool 64 causes the tether 60 to unwind from the spool 64.

The spool 64 can be equipped with provisions to rewind the tether 60 on the spool 64. This feature can be used to retrieve the device 10 if the device 10 becomes inoperable within the vessel 200, or to store the tether 60 as the device exits the vessel 200 in a normal manner. For example, a handle 65 can be attached to the spool 64 to rotate the spool 64. The spool 64 can also be rotated by a motor (not shown) mounted on the housing 62. The motor can be used in lieu of, or in addition to the handle 65. Moreover, a spring (not shown) can be connected to the housing 62 and the spool 64 to bias the spool 64 in the direction of winding so that the tether 60 is automatically rewound as the device 10 exits the vessel 200 in the normal manner, i.e., under its own power and steering.

The interior of the housing 62 can be purged with a suitable inert gas such as helium or nitrogen, to reduce the potential for the tether 60 to introduce contaminants into the vessel 200. The source of the purge gas can be located inside or outside of the housing 62. If necessary, the surface of the tether 60 can be cleaned using a solvent or other suitable means before the tether 60 is initially wound on the spool 64, to remove oil residue and other potential contaminants from the surface. In addition, the tether 60 can be wrapped or otherwise sheathed in a material that is compatible with the UHP ammonia (or other specialty material) which is to be stored within the vessel 200.

The cable 29 of the alternative device 10a can be used as a tether to retrieve the device 10a if the device 10 becomes inoperable within the vessel 200. The cable 29 can be stored and retracted using an arrangement that is substantially identical to the housing 62, spool 64, handle 65, and the optional motor and spring.

Figure 10:
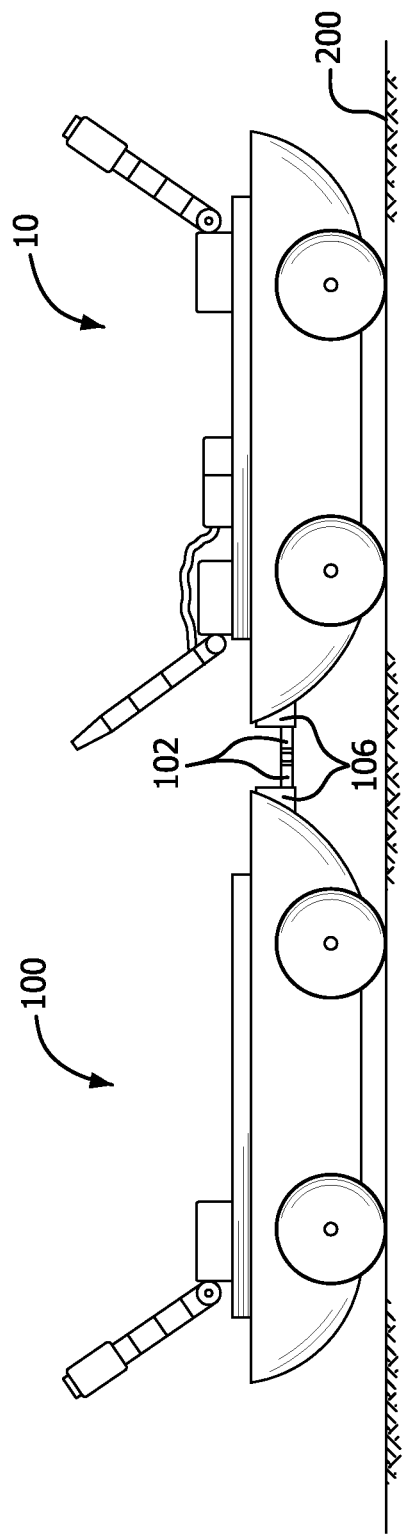
FIG. 10 is a side view of the device shown in FIGS. 1-4 and 8 mated with a rescue device and being retrieved by the rescue device from the vessel shown in FIG. 4.

The incapacitated device 10 can also be retrieved from the internal volume 202 of the vessel 200 using a rescue device 100 depicted in FIG. 10. The rescue device 100 can be another device 10, or another type of device suitable for use within the vessel 200, i.e., the rescue device 100 should be capable of operating within the vessel 200 without contaminating the UHP ammonia or other specialty material to be stored therein.

The device 10 and the rescue device 100 can include features the permit the device 10 and the rescue device 100 to be mated. The rescue device 100, once mated with the incapacitated device 10, can tow or push the device 10 out of the vessel 200 as shown in FIG. 10.

For example, the device 10 can include one or more magnets 102, as shown in FIGS. 1-3 and 10. The magnets 102 can be mounted on the shell 98 or at another suitable location on the device 10. The rescue device 100 can also include one or more of the magnets 102. The rescue device 100 can be maneuvered to place one of its magnets 102 proximate one of the magnets 102 of the device 10, so that the mutual attraction between the magnets 102 secures the magnets 102 to each other and causes the device 10 to remain attached to the rescue device 100 as the rescue device 100 tows or pushes the incapacitated device 10 out of the internal volume 202 of the vessel 200 as shown in FIG. 10.

The device 10 can include one or more mechanical couplers 106 such as hooks or latches, as shown in FIGS. 1-3 and 10. The couplers 106 can be used in lieu of the magnets 102. The device 10 is depicted with both the couplers 106 and the magnets 102 for illustrative purposes.

The couplers 106 can be mounted on the shell 98 or at another suitable location on the device 10. The rescue device 100 can also include one or more couplers 106 that mate with the couplers 106 on the device 10. The rescue device 100 can be maneuvered so that one of the couplers 106 thereon mates with one of the couplers 106 on the device 10. The mated couplers 106 cause the device 10 to remain attached to the rescue device 100 as the rescue device 100 tows or pushes the incapacitated device 10 out of the internal volume of the vessel 200 as shown in FIG. 10.

An incapacitated device 10 can be removed from the internal volume 202 of the vessel 200 using a cable with maneuvering capability in lieu of the rescue device 100. The maneuverable cable can be equipped with one of the magnets 102 or one of the couplers 106 mounted on or near an end of the cable. The end of the cable can be inserted into the internal volume 202 and maneuvered so that the magnet 102 on the cable engages one of the magnets 102 on the incapacitated device 10, or the coupler 106 on the cable engages one of the couplers 106 on the device 10. The cable can then be withdrawn from the vessel 200 to pull the incapacitated device 10 from the vessel 200.

The cable 29 of the alternative device 10a can be used to pull the device 10a from the internal volume 202 of the vessel 200 if the device 10a becomes incapacitated within the vessel 200, thereby eliminating the need for the rescue device 100 or the manipulable cable.

Alternative embodiments of the device 10 can be non-self-propelled, i.e., non-motorized. The non-motorized device can be pulled through the internal volume 202 of the vessel 200 using a cable such as the maneuverable cable discussed above. More particularly, a first end of the cable can be routed through the vessel 200 by way of the access openings 206. The first end can be secured to the device using the magnets 102 or couplers 106 discussed above, or other suitable means. The distal portion the cable, i.e., the portion of the cable 112 located on the opposite side of vessel 200 from the first end, can then be pulled to draw the device through the vessel 200.

Figure 11:
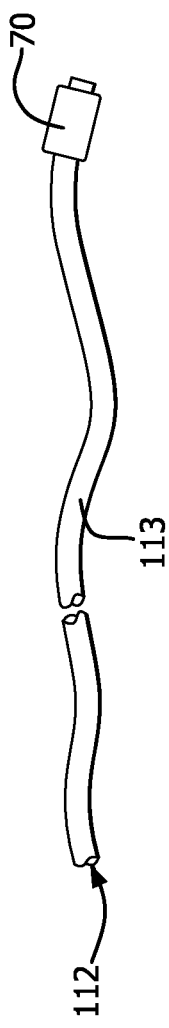
FIG. 11 is a side view of a cable having a camera mounted on an end thereof for performing inspections and other operations within the vessel depicted in FIG. 4.

In other alternative embodiments, an appropriate sensor such as the camera 70 can be attached to an end of a cable such as maneuverable cable 112 shown in FIG. 11. An inspection of the interior of the vessel 200 can be performed by inserting the end of the cable 112 and the attached camera 70 into the internal volume 202 of the vessel 200 by way of one of the access openings 206, and then manipulating the position of the camera 70 using the cable 112.

A cover or wrapping 113 can be placed over the cable 112, if necessary, to prevent debris and other potential contaminants generated by the cable 112 from being left in the internal volume 202 of the vessel 200. The cover or wrapping can be formed for a material that will not contaminate the UHP ammonia or other specialty product to be stored in the vessel 200.

The relatively compact size of the device 10 and the operator module 54 facilitates relatively easy shipping of the device 10 and the operator module 54. The device 10 can thus be used to inspect and repair vessels such as the vessel 200 in the field, i.e., at the vessels' point of use or other location away from the depot or other facility at which the vessels are filled, maintained, overhauled, etc. The device 10 can shipped in a case or container that maintains a blanket of non-contaminating gas around the device 10.

The device 10 can be sized to fit within the openings 206 that accommodate the pressure-relief valves 209 on the vessel 200, as noted above. Thus, the vessel 200 does not need to be provided with additional access openings to accommodate the device 10. Because access openings represent a potential source of leakage on the vessel 200, the use of the device 10 does not require the introduction of additional potential sources of leakage into the vessel 200.

Because the device 10 can reach substantially the entire internal volume 202 of the vessel 200 due to its maneuvering capability, the device 10 can be accommodated by a single access opening such as the opening 206.

Two of the openings 206 can be used to accommodate the device 10, however, if desired by the operator. For example, the device 10 can be inserted into the internal volume 202 by way of a first of the openings 206 located proximate a first end of the vessel 200, and removed from the internal volume 202 by way of a second opening 206 located proximate a second end of the vessel 200, so that the device 10 does not need to backtrack within the internal volume 202 to return to the first opening 206.

Alternatively, the two openings 206 can each be used as both an entrance and an exit point for the device 10, i.e., a portion of the interior volume 202 of the vessel 200 can be accessed by the device 10 by way of a first of the openings 206, and the remainder of the internal volume 202 can be accessed by way of the other opening 206. The procedure can be used, for example, if an obstacle is present within the internal volume 202 at some point between the two openings 206.

The internal volume 200 can be purged with a non-contaminating gas or blend of gases while the safety-relief valve 209 is removed from the vessel 200 to accommodate the device 10, to prevent infiltration of ambient air into the internal volume 202. For example, in applications where the vessel 200 is to be used to hold UHP ammonia, a nitrogen purge can be maintained in the internal volume 200 because nitrogen is generally considered non-contaminating with respect to UHP ammonia.

The use of a nitrogen purge or any other type of oxygen-deficient atmosphere presents an asphyxiation hazard when human entry into the purged volume is required. Moreover, the breathing equipment required for use in an oxygen-deficient environment is generally unsuitable for use in volumes that will hold HP or UHP materials. The use of the device 10 can eliminate the need for human entry into the internal volume 202, and can thus eliminate the safety and contamination issues associated with such entry.

Moreover, vessels used to hold hazardous materials usually must be subjected to a decontamination process before a human can enter the vessel for inspection or other purposes. The device 10, by eliminating the need to human entry into such vessels, can eliminate the need for such decontamination.

Eliminating the need to send a human into the vessel 200 can eliminate the need for a manway in the vessel 200. (The vessel 200 is depicted without a manway, for clarity of illustration.) A typical manway is relatively large, e.g., 2.5-feet in diameter, to facilitate the passage of a human therethrough, and the corresponding manway cover likewise is relatively large. Eliminating the relatively large manway cover can thus result in a significant reduction in the weight of the vessel 200. For example, the manway cover can have a thickness "S1" of about 2.0 inches and a diameter "D1" of approximately 2.5 feet; and the shell of the vessel 200 can have a thickness of about 0.5 inch. The density of the material from which the manway cover is formed can have a density of about 500 pounds per cubic foot. The weight of the manway cover can be calculated as $\pi \times ((D1^2)/4) \times S1 \times density$=about 409 pounds.

Eliminating the manway cover, in effect, replaces the 2.0-inch thick manway cover with a section of the 0.5-inch-thick shell. The weight of the shell section can be calculated using the above equation, and substituting the 0.5-inch thickness of the shell for the 2.0-inch thickness of the manway. The resulting weight of the shell section is about 307 pounds, or about 102 pounds lighter than the manway. Additional weight savings may be achieved by the elimination of the fasteners, flanges, and other hardware used to fasten and seal the manway cover. Moreover, the internal volume 202 of the vessel 200 can potentially be increased by eliminating the manway and the hardware associated therewith.

Reducing the weight and increasing the internal volume 202 of the vessel 200 can increase the overall amount of material that can be carried in the vessel 200, which in turn can lead to increased revenue for the provider of the material. Fabrication costs can also potentially be reduced by eliminating the manway.

Furthermore, it is more difficult, in general, to seal a relatively large opening than a small opening in a vessel such as the vessel 200. Moreover, sealing difficulties can be exacerbated in transportable vessels due to the vibrations, bumps, and temperature swings associated with the transportation process. Thus, eliminating the relatively large manway and its associated cover can substantially reduce the potential for leakage in the vessel 200.

Eliminating the need for human access to the internal volume 202 can lead to the elimination or modification of other features on the vessel 200. For example, the size and thickness of the emergency response lid on the valve box (where required) of the vessel 200 may be reduced, and the structural integrity of the valve box may be relaxed if human access to the internal volume 202 is not required, leading to further overall weight reductions in the vessel 200.

Reducing the weight and increasing the internal volume of the vessel 202 can increase the overall amount of material that can be carried in the vessel 200, which in turn can lead to increased revenue for the vendor and/or shipper of the material.

The device 10 can be introduced into and operated within the internal volume 202 of the vessel 200 while the internal volume 200 is maintained at the static vapor pressure of the UHP ammonia or other material that has been held in the vessel 200. This manner of operation can eliminate the expense and set-up time associated with purging the internal volume 202 with nitrogen or another non-contaminating material.

Figure 12:
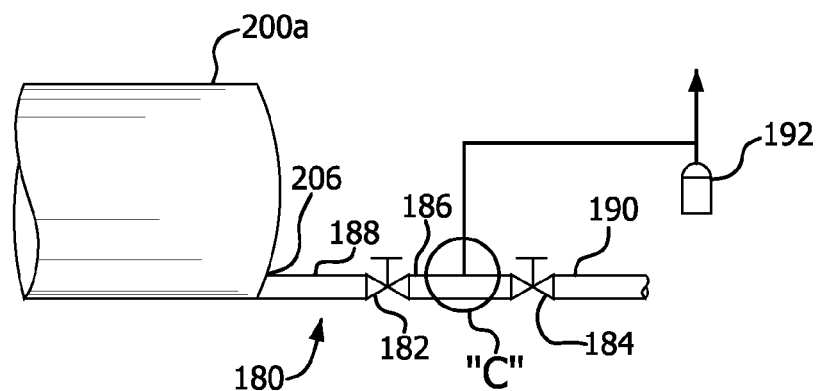
FIG. 12 is a side view of an alternative embodiment of the vessel depicted in FIG. 4, the alternative embodiment having a valving system that isolates the internal volume of the vessel from the ambient environment as the device shown in FIGS. 1-4 and 8 is inserted into and retrieved from the internal volume.

For example, FIG. 12 depicts a valving system 180 that permits the device 10 to be introduced into and removed from an internal volume of a vessel 200a while maintaining the HP, UHP, or other material within the vessel 200a at a stagnant vapor pressure. The vessel 200a can be substantially identical to the vessel 200, with the exception of the system 180.

The system 180 comprises a first valve 182 and a second valve 184. The system 180 also comprises a first conduit 186 that connects the first and second valves 182, 184; and a second conduit 188 that connects the first valve 182 and the vessel 200a. The system 180 also comprises a third conduit 190 connected to the second valve 184. The system 180 further comprises a purging device 192 connected to the first conduit 186.

Figure 13:
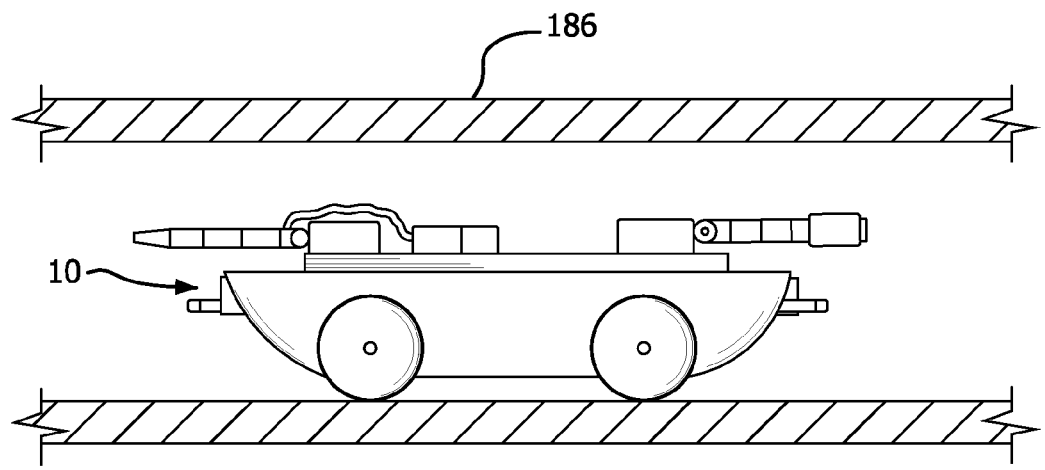
FIG. 13 is a magnified view of the area designated "C" in FIG. 12, depicting a conduit of the valving system in cross section to reveal the device shown in FIGS. 1-4 and 8 inside of the conduit.

The device 10 can be introduced into the internal volume of the vessel 200a by way of the valving system 180 by opening the second valve 184 while the first valve 182 is in its closed position, and inserting the device 10 into the first conduit 186 by way of the third conduit 190 and the second valve 184, as shown in FIG. 13.

The second valve 184 can then be closed, and the purging device 192 can be activated to purge the volume within the first conduit 186 of any ambient air that may have infiltrated into first conduit 186 as the device 10 was introduced therein. The purging device 190 can effectuate the purge by, for example, evacuating the volume within the second conduit 186 using a vacuum, and then filling the volume with a gas that will not contaminate the UHP ammonia or other specialty material within the internal volume of the vessel 200a.

The first valve 182 can be opened once the purge has been completed, and the device 10 can be maneuvered into the internal volume of the vessel 200a under its own power by way of the first valve 182 and the second conduit 188. The first valve 182 can subsequently be closed to reduce the potential for leakage into or out of the internal volume.

The device 10 can be removed from the internal volume of the vessel 200a by opening the first valve 182, and maneuvering the device 10 into the first conduit 186 by way of the second conduit 188 and the first valve 182. The first valve 182 can then be closed. If desired, the volume within the first conduit 186 can be purged of the material from within the vessel 200a and filled with ambient air using the purging device 192. This step may be required if the material within the vessel 200a is a hazardous material.

The second valve 184 can subsequently be opened, and the device 10 can be maneuvered out of the valving system 180 by way of the second valve 184 and the third conduit 190.

The foregoing description is provided for the purpose of explanation and is not to be construed as limiting the invention. Although the invention has been described with reference to preferred embodiments or preferred methods, it is understood that the words which have been used herein are words of description and illustration, rather than words of limitation. Furthermore, although the invention has been described herein with reference to particular structure, methods, and embodiments, the invention is not intended to be limited to the particulars disclosed herein, as the invention extends to all structures, methods and uses that are within the scope of the appended claims. Those skilled in the relevant art, having the benefit of the teachings of this specification, can make numerous modifications to the invention as described herein, and changes may be made without departing from the scope and spirit of the invention as defined by the appended claims.

The invention claimed is:

1. A system comprising:
   a) a vessel having an internal volume and configured to store an ultra high purity fluid, the vessel comprising: a valve system comprising a first valve and a second valve connected by a first conduit; a second conduit that connects the first valve and the vessel; a third conduit connected to the second valve; and a purging device connected to the first conduit; and
   b) a device capable of entering the interior of the vessel, the device comprising: a body; a sensor mounted on the body; at least one of a transmitter for transmitting the information from the device and a memory-storage device for storing the information; a shell that at least partially encloses the body; at least one wheel and/or roller formed from a material that does not reduce the purity of the fluid below a predetermined minimum when the material comes into contact with the fluid; and at least one electric motor and at least one drive axle for driving the at least one wheel and/or roller,
   wherein device is inserted into the internal volume by way of the valve system by opening the second valve while the first valve is in a closed position, and inserting the device into the first conduit by way of the third conduit and the second valve.

2. The system of claim 1 wherein the shell is formed from a material that does not reduce the purity of the fluid below the predetermined minimum when the fluid is exposed to the material from which the shell is formed.

3. The system of claim 1, further comprising an operator console located outside of the vessel and communicatively coupled to the device and comprising a controller for generating directional inputs for the device.

4. The system of claim 3 wherein the device further comprises a telemetry system for transmitting information between the device and the operator console.

5. The system of claim 2 wherein the shell is capable of catching debris and particulate matter from other parts of the device.

6. The system of claim 1 wherein the device further comprises a cable for transmitting electric power to the device from a power source located outside of the vessel.

7. The system of claim 1 wherein the purging device is capable of purging the first conduit of any ambient air that may have infiltrated into first conduit after the device is introduced therein.

8. The system of claim 1 wherein the device further comprises a vacuum pickup movably connected to the body, and a vacuum source in fluid communication with the vacuum pickup.

9. The system of claim 1 wherein the device further comprises a nozzle movably connected to the body, and a reservoir of filler material in fluid communication with the nozzle.

10. The system of claim 1 wherein the device further comprises a microprocessor.

11. The system of claim 10 wherein the microprocessor controls the operation of the at least one motor to effectuate movement of the device in a desired direction.

12. The system of claim 10 wherein the device has two motors.

13. The system of claim 1 wherein the device further comprises a video camera.

14. The system of claim 1 wherein the device is equipped with a collecting means for collecting material from the interior of the vessel.

15. The system of claim 14 wherein the collecting means comprises a vacuum source.

16. The system of claim 1 wherein the device further comprises a stationary or movable arm for moving suspected particulate matter.

17. The system of claim 1 wherein the device further comprises a vacuum line in fluid communication with a vacuum source located outside the vessel.

18. The system of claim 1 wherein the device further comprises at least one magnet.

19. The system of claim 1 wherein the device further comprises at least one mechanical coupler.

* * * * *